(12) United States Patent
Sheng et al.

(10) Patent No.: US 6,649,390 B1
(45) Date of Patent: Nov. 18, 2003

(54) THERMOPHILIC ALKALINE PHOSPHOESTERASE AND ITS EXPRESSION

(75) Inventors: Xiaoyu Sheng, Shanghai (CN); Yumin Mao, Shanghai (CN); Youzhong Yuan, Shanghai (CN); Chaoneng Ji, Shanghai (CN); Zongxiang Zhou, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 09/530,851

(22) PCT Filed: Nov. 13, 1998

(86) PCT No.: PCT/CN98/00272

§ 371 (c)(1),
(2), (4) Date: May 4, 2000

(87) PCT Pub. No.: WO99/27115

PCT Pub. Date: Jun. 3, 1999

(30) Foreign Application Priority Data

Nov. 13, 1997 (CN) ........................................ 97106724 A

(51) Int. Cl.$^7$ ............................. C12N 9/16; C12N 9/14; C12N 9/12; C12N 1/20; C07H 21/04
(52) U.S. Cl. ........................ 435/196; 435/195; 435/194; 435/252.3; 435/320.1; 536/23.2
(58) Field of Search ................................. 435/196, 195, 435/194, 252.3, 320.1; 536/23.2

(56) References Cited

PUBLICATIONS

Tercero et al., "The Biosynthetic Pathway of the Aminonucleoside Antibiotic puromycin, as Deduced from the Molecular Analysis of the pur Cluster of *Streptomyces alboniger*", J. Biol. Chem., vol. 271, No. 3, Jan. 19, 1996, pp. 1579–1590.

Yamagishi et al, "Pyrimidine biosynthesis genes (pyrE and pyrF) of an extreme thermophile, Thermus terjmophilus", Appl. Enviorn, Microbiol., vol. 62, No. 6, Jun. 1996, pp. 2191–2194.

GenBank, AF079878, Aug. 11, 1998, 2 pages.

Hulett et al., "*Bacillus subtilis* Alkaline Phosphatases II and IV—Cloning, Sequencing and Comparisons of Deduced Amino Acid Sequence with *Escherichia coli* Alkaline Phosphate Three–Dimensional Structure", The Journal of Biological Chemistry, vol. 266, No. 2, pp. 1077–1084, 1991.

Jablonski et al., "Preparation of oligodeoxynucleotide—alkaline phosphatase conjugates and their use as hybridization probes", Nucleic Acids research, vol. 14, No. 15, pp. 6115–6129.

Schauder et al., "Short Communications—Inducible expression vectors incorporating the *Escherichia coli* atpE translational initiation region", Gene, 52 (1987), pp. 279–283.

Schaap et al., "Chemiluminescent Substrates for Alkaline Phosphatase: Application to Ultrasensitive Enzyme–Linked Immunoassays and DNA Probes", Clinial Chemistry, vol. 35, No. 9., 1983, pp. 1863–1864.

Garattini et al., "Cloning and sequencing of bovine kidney alkaline phosphatase cDNA", Gene, 59 (1987) pp. 41–46.

Misumi et al., "Primary structure of rat liver alkaline phosphatase deduced from its cDNA", Biochem. J., (1988), 249:661–668.

Yamagishi et al., "Pyrimidine Biosynthesis Genes (pyrE and pryF) of an Extreme Thermophile, *Thermus thermophilus*", Applied and Environmental Microbiology, vol. 62, No. 6, Jun. 1996, pp. 2191–2194.

*Primary Examiner*—Tekchand Saidha
(74) *Attorney, Agent, or Firm*—Baker Botts L.L.P.

(57) ABSTRACT

The invention belongs to the field of biological engineering techniques and relates to a thermophilic alkaline phosphoesterase. The invention provides an amino acid sequence of a thermophilic alkaline phosphoesterase of the invention, as well as a DNA fragment encoding the amino acid sequence. The present invention also includes methods for cloning an expression vector containing the DNA fragment or a portion thereof and for producing the recombinant enzyme. The invention also relates to a method for tagging biological macromolecules utilizing the enzyme.

5 Claims, 6 Drawing Sheets

```
GCC TTC CCA GGG TCA CGG GGT CAT TAT CCC CTG ACC TTC CCC TGA CTT GCG CTC         54

CTT ACT TTG AAC TCG GAG GTG AGA AGC ATG AAG CGA AGG GAC ATC CTG AAA GGT        108
                                Met Lys Arg Arg Asp Ile Leu Lys Gly

GGC CTG GCT GCG GGG GCC CTG GCC CTC CTG CCC CGG GGG CAT ACC CAG GGG GCT        162
Gly Leu Ala Ala Gly Ala Leu Ala Leu Leu Pro Arg Gly His Thr Gln Gly Ala

CTG CAG AAC CAG CCT TCC TTG GGA AGG CGG TAC CGC AAC CTC ATC GTC TTC GTC        216
Leu Gln Asn Gln Pro Ser Leu Gly Arg Arg Tyr Arg Asn Leu Ile Val Phe Val

TAC GAC GGG TTT TCC TGG GAG GAC TAC GCC CAG GCC ATC GCC TAC GCC CGG AGG        270
Tyr Asp Gly Phe Ser Trp Glu Asp Tyr Ala Ile Ala Gln Ala Tyr Ala Arg Arg

CGG CAG GGC CGG GTT CTC GCC CTG GAG CGC CTC CTC GCC CGC TAC CCC AAC GGG        324
Arg Gln Gly Arg Val Leu Ala Leu Glu Arg Leu Leu Ala Arg Tyr Pro Asn Gly

CTC ATC AAC ACC TAC AGC CTC ACC AGC TAC GTC ACC GAG TCC AGC GCC GCG GGG        378
Leu Ile Asn Thr Tyr Ser Leu Thr Ser Tyr Val Thr Glu Ser Ser Ala Ala Gly

AAC GCC TTC TCC TGC GGG GTG AAG ACG CTC AAG GGG GGG CTC GCC ATC CAC GCC        432
Asn Ala Phe Ser Cys Gly Val Lys Thr Leu Lys Gly Gly Leu Ala Ile His Ala

GAC GGG ACC CCC CTC AAG CCC TTC TTC GCC GCG AAG GAG GCG GGG AAG GCC            486
Asp Gly Thr Pro Leu Lys Pro Phe Phe Ala Ala Ala Lys Glu Ala Gly Lys Ala
```

FIG. 1A

```
GTG GGG CTC GTG ACC ACC GTC ACC CAC CCG GCG AGC TTC GTG        540
Val Gly Leu Val Thr Thr Val Thr His Ala Thr Pro Ala Ser Phe Val

GTG TCC AAT CCC GAC CGG AAC GCC GAG GAG ATC GCC GAG CAG TAC CTG GAG        591
Val Ser Asn Pro Asp Arg Asn Ala Glu Glu Ile Ala Glu Gln Tyr Leu Glu

TTC GGG GCC GAG GTG TAC CTT GGG GGC GGG GAC CGC TTT TTC AAC CCC GCC AGG    648
Phe Gly Ala Glu Val Tyr Leu Gly Gly Gly Asp Arg Phe Phe Asn Pro Ala Arg

CGC AAG GAC GGG AAG GAC CTC TAC GCC CTC GCC TTC GCC AAG GGG TAC GGG GTG    702
Arg Lys Asp Gly Lys Asp Leu Tyr Ala Leu Ala Phe Ala Lys Gly Tyr Gly Val

GTG CGC ACC CCC GAG GAG CTC GCC CGT TCC AAC GCC ACC CGG CTC CTG GGC GTC    756
Val Arg Thr Pro Glu Glu Leu Ala Arg Ser Asn Ala Thr Arg Leu Leu Gly Val

TTC GCC GAC GGC CAC GTG CCC TAC GAG ATT GAC CGC CGG TTC CAG GGC CTT GGG    810
Phe Ala Asp Gly His Val Pro Tyr Glu Ile Asp Arg Arg Phe Gln Gly Leu Gly

GTG CCC AGC CTC AAG GAA ATG GTC CAG GCC GCT TTG CCC CGG CTT GCC GCC CAC    864
Val Pro Ser Leu Lys Glu Met Val Gln Ala Ala Leu Pro Arg Leu Ala Ala His

CGC GGG GGC TTC GTC CTT CAG GTG GAA GCG GGG CGG ATT GAC CAC GCC AAC CAT    918
Arg Gly Gly Phe Val Leu Gln Val Glu Ala Gly Arg Ile Asp His Ala Asn His
```

FIG. 1B

```
TTG AAC GAC GCC GGG GCC ACC CTT TGG GAC GTG CTG GCG GCG GAC GAG GTC TTG      972
Leu Asn Asp Ala Gly Ala Thr Leu Trp Asp Val Leu Ala Ala Asp Glu Val Leu

GAG CTT CTC ACC GCC TTC GTG GAC CGG AAC CCG GAC ACC CTC CTC GTG GTC         1026
Glu Leu Leu Thr Ala Phe Val Asp Arg Asn Pro Asp Thr Leu Leu Val Val

TCG GAC CAC GCC ACC GGG GTG GGC GCC CTC TAC GGG CGG AGC TAC CTG             1080
Ser Asp His Ala Thr Gly Val Gly Ala Leu Tyr Gly Arg Ser Tyr Leu

GAG AGC TCC GTG GGC ATT GAC CTC CTG GGG GCG CAA AAG GCC AGC TTT GAG TAC     1134
Glu Ser Ser Val Gly Ile Asp Leu Leu Gly Ala Gln Lys Ala Ser Phe Glu Tyr

ATG CGC CGT GTC TTG GGC TCG GCC CCC GAT GCT GCA ACG GAC GAG GCG CAG ATG GTG GTC TAC  1188
Met Arg Arg Val Leu Gly Ser Ala Pro Asp Ala Ala Thr Asp Glu Ala Gln Met Val Val Tyr

CAG ACC CTG AAG GGG GTC TCC CTC ACG GAC TGG CCT GAT GCC GTG CGC CAG GGC ATC CAG CCC  1242
Gln Thr Leu Lys Gly Val Ser Leu Thr Asp Trp Pro Asp Ala Val Arg Gln Gly Ile Gln Pro

GCC ATC CGC GAG CGG GTC TAC TGG CCT GAT GCC GTG CGC CAG GGC ATC CAG CCC     1296
Ala Ile Arg Glu Arg Val Tyr Trp Pro Asp Ala Val Arg Gln Gly Ile Gln Pro

GAA AAC ACC ATG GCC ATG GTG CAG AAG AAC GCC AGC AAG CCC GAC CGG             1350
Glu Asn Thr Met Ala Met Val Gln Lys Asn Ala Ser Lys Pro Asp Arg
```

FIG. 1C

```
CCC AAC ATC GGC TGG AGC TCT GGG CAG CAC ACG GCG AGC CCC GTC ATC CTC CTC    1404
Pro Asn Ile Gly Trp Ser Ser Gly Gln His Thr Ala Ser Pro Val Ile Leu Leu

CTC TAC GGC CAG GGC CTG CGC TTC GTC CAG CTT GGC CTG GTG GAC AAC ACC CAC    1458
Leu Tyr Gly Gln Gly Leu Arg Phe Val Gln Leu Gly Leu Val Asp Asn Thr His

GTG TTC CGC CTG ATG GGC GAG GCC CTG AAC CTC CGC TAC CAG AAC CCG GTG ATG    1512
Val Phe Arg Leu Met Gly Glu Ala Leu Asn Leu Arg Tyr Gln Asn Pro Val Met

AGC GAG GAG GCC CTG GAG ATC CTC AAG GCC AGG CCC CAG GGG ATG CGC CAC        1566
Ser Glu Glu Ala Leu Glu Ile Leu Lys Ala Arg Pro Gln Gly Met Arg His

CCC GAG GAC GTC TGG GCC TAA GGG CGG GTC GCG GGA TCG GCC GGG GCC GGT TGG    1620
Pro Glu Asp Val Trp Ala  *

GGT CCG GAG CCG TGG CTT CCT GGG CGG GAA CCT TGC CCC CGC CGA                1674
GGC AGG GCC GCC CCA GGT CCA GGA CCT GAG CCG CCT CGG CCA AAA                1728
GGG CGT CCT TCA CCT GGC CCA GGT CCC GGT AGC GGC GGA GGG GGT TTT GGG        1782
GGA CGA TCC CCA TCC CCA CGA CCT CGT TGG AGA CCC TCT TGC CGC TTT            1836
CCT CCA CCG CGC TTA GGA AGC CGG CGA TGA GGG GGT CCA GGC CCC GTT            1890
CCA TCA GGT TGG CGA ACC CAG GTG AGG CAG TCC ACC ACG GTG GGG TGG            1944
CGG GCC CTC TTT AGG GCC CCC GGG AGG TCC TCC AGG GTC TCC CAG                1998
GTG GGG CGC GGG TGG TCC TGG GCG GCG GA                                     2030
```

FIG. 1D

THERMOPHILIC ALKALINE PHOSPHOESTERASE AND ITS EXPRESSION

The present invention belongs to the biotechnology field and relates to a thermophilic alkaline phosphatase (or phosphoesterase).

The alkaline phosphatase is an important enzyme, which is widely distributed in various organisms, and participates in cellular phosphorus metabolism. The alkaline phosphatase is a non-specific phosphomonoesterase, which produces a phosphoserine intermediate and finally produces inorganic phosphorus and alcohol. The amino acid sequences and the corresponding genes of the alkaline phosphatase have been obtained from many prokaryote and eukaryote, such as E.Coli, B. subtilis, yeast, calf intestine, human placenta, etc. (J Bio Chem. 1991, 266: 1077–84).

The alkaline phosphatase is an important enzyme tool in the molecular biology study. It can be used in dephosphorization of the termini of DNA or RNA fragment in gene cloning, as a reagent for enzyme-linked assay in immunology research, and as a label for nucleic acid hybridization or detection of the PCR products.

Nucleic acid hybridization, one of the most extensive applied techniques in molecular biology, is a technique that detects the complementary nucleotide sequences by using the labeled DNA or RNA fragment as a probe. Typically, the label of the nucleotide probe is an isotope, such as $^{32}P$ or $^{35}S$. Though the isotope label is very sensitive, its conventional biological and medical application and commercial kits are substantially restricted by the short half-life, the danger to the operator during the manipulating procedure, and the trouble of dealing with the isotopic wastes, etc. People have extensively studied the labeling of the nucleotide probe with the non-isotopic materials during the last decade (Mattews J. Anal Biochem.1988, 169:1–25).

For the time being, the common labels include enzyme, fluorescein, biotin, digoxin (Europe Patent EP 304934). The labeling methods can be divided into direct and indirect techniques based on whether the label can be detected directly or not after hybridization. The major indirect labels are haptens, such as biotin and digoxin; and the major direct labels are enzymes and fluoresceines. The alkaline phosphatase is the most extensively applied enzyme in both direct and indirect labeling methods. In the 1980's, the direct nucleotides labeling using the alkaline phosphatase was reported (Jablonski E: Nucleic Acid Res. 1986, 14: 6115~6128). The enzymes described in the reports were mainly calf intestine alkaline phosphatase and E.Coli alkaline phosphatase. These alkaline phosphatases have a main drawback of being instable under high temperature, thus not suitable for hybridization in higher temperature. However, the hybridization under higher temperature is usually beneficial for reducing the background and enhancing the specificity. Additionally, these enzymes can not tolerate the strong hybridization and elution conditions, such as high concentration of SDS. Because of the poor thermostability, the oligonucleotides directly labeled by these alkaline phosphatases can not be used as the primers for the polymerase chain reaction (PCR).

The thermophilic bacteria are microorganisms that can live and grow at more than 55° C. Most enzymes in thermophilic bacteria, such as the thermophilic DNA polymerase used extensively in PCR, are thermophilic enzymes that have high application value. But there was no report or patent about the alkaline phosphatase from thermophilic bacteria before the present invention.

SUMMARY OF THE INVENTION

The present invention provides an alkaline phosphoesterase which has higher thermostability and is suitable for extensive use.

As used in this invention, the term "thermophilic alkaline phosphatase" ("FD-TAP" for short) means the enzyme with the following features or characteristics: its optimum reaction temperature is above 50° C., and its enzyme activity remains at least 70% after the incubation at 70° C. for 30 mins. As far as the same enzyme is concerned, the features or characteristics described above are observed under optimal preservation conditions and reaction systems. The features or characteristics might fluctuate as the conditions or reaction systems change.

The present invention provides a thermophilic alkaline phosphatase that is homologous or substantially homologous to the amino acid sequence shown in Table 1 (SEQ ID NO:2).

TABLE 1

The amino acid sequence of the thermophilic alkaline phosphatase

```
  1  Met Lys Arg Arg Asp Ile Leu Lys Gly Gly Leu Ala Ala Gly Ala
 16  Leu Ala Leu Leu Pro Arg Gly His Thr Gln Gly Ala Leu Gln Asn
 31  Gln Pro Ser Leu Gly Arg Arg Tyr Arg Asn Leu Ile Val Phe yaI
 46  Tyr Asp GIy Phe Ser Trp Glu Asp Tyr Ala Ile Ala Gln Ala Tyr
 61  Ala Arg Arg Arg Gln Gly Arg Val Leu Ala Leu Glu Arg Leu Leu
 76  Ala Arg Tyr Pro Asn Gly Leu Ile Asn Thr Tyr Ser Leu Thr Ser
 91  Tyr Val Thr Glu Ser Ser Ala Ala GIy Asn Ala Phe Ser Cys Gly
106  Val Lys Thr Val Asn Gly Gly Leu Ala Ile His Ala Asp Gly Thr
121  Pro Leu Lys Pro Phe Phe Ala Ala Ala Lys Glu Ala Gly Lys Ala
136  Val Gly Leu Val Thr Thr Thr Thr Val Thr His Ala Thr Pro Ala
151  Ser Phe Val Val Ser Asn Pro Asp Arg Asn Ala Glu Glu Arg Ile
166  Ala Glu Gln Tyr Leu GIu Phe Gly Ala Glu Val Tyr Leu Gly Gly
181  Gly Asp Arg Phe Phe Asn Pro Ala Arg Arg Lys Asp Gly Lys Asp
196  Leu Tyr Ala Ala Phe Ala Ala Lys Gly Tyr Gly Val Val Arg Thr
211  Pro Glu Glu Leu Ala Arg Ser Asn Ala Thr Arg Leu Leu Gly Val
226  Phe Ala Asp GIy His Val Pro Tyr Glu Ile Asp Arg Arg Phe Gln
241  Gly Leu Gly Val Pro Ser Leu Lys Glu Met Val Gln Ala Ala Leu
256  Pro Arg Leu Ala Ala His Arg Gly Gly Phe Val Leu Gln Val Glu
271  Ala Gly Arg Ile Asp His Ala Asn His Leu Asn Asp Ala Gly Ala
286  Thr Leu Trp Asp Val Leu Ala Ala Asp Glu Val Leu Glu Leu Leu
301  Thr Ala Phe Val Asp Arg Asn Pro Asp Thr Leu Leu Leu Val Val
316  Ser Asp His Ala Thr Gly Val Gly Ala Leu Tyr Gly Ala Gly Arg
331  Ser Tyr Leu Glu Ser Ser Val Gly Ile Asp Leu Leu Gly Ala Gln
346  Lys Ala Ser Phe Glu Tyr Met Arg Arg Val Leu Gly Ser Ala Pro
361  Asp Ala Ala Gln Val Lys Glu Ala Tyr Gln Thr Leu Lys Gly Val
```

TABLE 1-continued

The amino acid sequence of the thermophilic alkaline phosphatase

| | | | | | | | | | | | | | | |
|---|---|---|---|---|---|---|---|---|---|---|---|---|---|---|
| 376 | Ser | Leu | Thr | Asp | Glu | Glu | Ala | Gln | Met | Val | Val | Arg | Ala | Ile | Arg |
| 391 | Glu | Arg | Val | Tyr | Trp | Pro | Asp | Ala | Val | Arg | Gln | Gly | Jle | Gln | Pro |
| 406 | Glu | Asn | Thr | Met | Ala | Trp | Ala | Met | Val | Gln | Lys | Asn | Ala | Ser | Lys |
| 421 | Pro | Asp | Arg | Pro | Asn | Ile | Gty | Trp | Ser | Ser | Gly | Gln | His | Thr | Ala |
| 436 | Ser | Pro | Val | Ile | Leu | Leu | Leu | Tyr | Gly | Gln | Gly | Leu | Arg | Phe | Val |
| 451 | Gln | Leu | Gly | Leu | Val | Asp | Asn | Thr | His | Val | Phe | Arg | Leu | Met | Gly |
| 466 | Glu | Ala | Leu | Asn | Leu | Arg | Tyr | Gln | Asn | Pro | Val | Met | Ser | Glu | Glu |
| 481 | Glu | Ala | Leu | Glu | Ile | Leu | Lys | Ala | Arg | Pro | Gln | Gly | Met | Arg | His |
| 496 | Pro | Glu | Asp | Val | Trp | Ala | | | | | | | | | |

The signal peptide composed of 26 amino acid residues is underlined at the N-terminus of the amino acid sequence.

The present invention further provides DNA fragments which are homologous or substantially homologous to the nucleotide sequence as shown in Table 2 which encodes the enzyme of the invention.

TABLE 2

The nucleotide sequence of the thermophilic alkaline phosphatase gene

```
   1 ATG AAG CGA AGG GAC ATC CTG AAA GGT GGC CTG GCT GCG GGG GCC
  46 CTG GCC CTC CTG CCC CGG GGC CAT ACC CAG GGG GCT CTG CAG AAC
  91 CAG CCT TCC TTG GGA AGG CGG TAC CGC AAC CTC ATC GTC TTC GTC
 136 TAC GAC GGG TTT TCC TGG GAG GAC TAC GCC ATC GCC CAG GCC TAC
 181 GCC CGG AGG CGG CAG GGC CGG GTT CTC GCC CTG GAG CGC CTC CTC
 226 GCC CGC TAC CCC AAC GGG CTC ATC AAC ACC TAC AGC CTC ACC AGC
 271 TAC GTC ACC GAG TCC AGC GCC GCG GGG AAC GCC TTC TCC TGC GGG
 316 GTG AAG ACG GTG AAC GGG GGG CTC GCC ATC CAC GCC GAC GGG ACC
 361 CCC CTC AAG CCC TTC TTC GCC GCG GCC AAG GAG GCG GGG AAG GCC
 406 GTG GGG CTC GTG ACC ACC ACC ACC GTC ACC GCC ACC CCG GCG
 451 AGC TTC GTG GTG TCC AAT CCC GAC CGG AAC GCC GAG GAG AGG ATC
 496 GCC GAG CAG TAC CTG GAG TTC GGG GCC GAG GTG TAC CTT GGG GGC
 541 GGG GAC CGC TTT TTC AAC CCC GCC AGG CGC AAG GAC GGG AAG GAC
 586 CTC TAC GCC GCC TTC GCC GCC AAG GGG TAC GGG GTG GTG CGC ACC
 631 CCC GAG GAG CTC GCC CGT TCC AAC GCC ACC CGG CTC CTG GGC GTC
 676 TTC GCC GAC GGC CAC GTG CCC TAC GAG ATT GAC CGC CGC TTC CAG
 721 GGC CTT GGG GTG CCG AGC CTC AAG GAA ATG GTC CAG GCC GCT TTG
 766 CCC CGG CTT GCC GCC CAC CGC GGG GGC TTC GTC CTT CAG GTG GAA
 811 GCG GGG CGG ATT GAC CAC GCC AAC CAT TTG AAC GAC GCC GGG GCC
 856 ACC CTT TGG GAC GTG CTG GCG GCG GAC GAG GTC TTG GAG CTT CTC
 901 ACC GCC TTC GTG GAC CGG AAC CCG GAC ACC CTC CTC CTC GTG GTC
 946 TCG GAC CAC GCC ACC GGG GTG GGG GCC CTC TAC GGG GCG GGC CGG
 991 AGC TAC CTG GAG AGC TCC GTG GGC ATT GAC CTC CTG GGG GCG CAA
1036 AAG GCC AGC TTT GAG TAC ATG CGC CGC GTC TTG GGC TCG GCC CCC
1081 GAT GCT GCC CAG GTG AAG GAG GCC TAC CAG ACC CTG AAG GGG GTC
1126 TCC CTC ACG GAC GAG GAG GCG CAG ATG GTG GTC CGG GCC ATC CGC
1171 GAG CGG GTC TAC TGG CCT GAT GCC GTG CGC CAG GGC ATC CAG CCC
1216 GAA AAC ACC ATG GCC TGG GCC ATG GTG CAG AAG AAC GCC AGC AAG
1261 CCC GAC CGG CCC AAC ATC GGC TGG AGC TCT GGG CAG CAC ACG GCG
1306 AGC CCC GTC ATC CTC CTC CTC TAC GGC CAG GGC CTG CGC TTC GTC
1351 CAG CTT GGC CTG GTG GAC AAC ACC CAC GTG TTC CTC CTG ATG GGC
1396 GAG GCC CTG AAC CTC CGC TAC CAG AAC CCG GTG ATG AGC GAG GAG
1441 GAG GCC CTG GAG ATC CTC AAG GCC AGG CCC CAG GGG ATG CGC CAC
1486 CCC GAG GAC GTC TGG GCC TAA
```

As used herein, the phrase "DNA fragment(s)" described above includes single- or double-stranded DNA.

Based on the specific circumstance, the term "homologous" means that (1) a DNA fragment has the identical nucleotide sequence when comparing with another DNA fragment; or (2) a protein has the identical amino acid sequence when comparing with another protein.

The term "substantially homologous" means that: (1) compared with another DNA fragment, a DNA fragment has enough identical nucleotide sequence so that the translated protein has the same or similar features or characteristics; (2) compared with another protein, a protein has enough identical amino acid sequence, so that both proteins have the same or similar features or characteristics.

There are various organisms, such as prokaryote, yeast and mammals, which can be used as the resources for the thermophilic alkaline phosphatase or its DNA. Preferably, said organism is a prokaryote, especially the thermophilic bacteria, such as the commercially available bacteria *Thermus thermophilus*.

One can make the DNA fragment encoding the thermophilic alkaline phosphatase partially deleted by using the genetic engineering techniques. Serial deletions can be made from 5' terminus to 3' terminus or from 3' terminus to 5' terminus of the DNA fragment. Alternatively, the DNA fragment can be deleted sequentially from both ends to the center. In addition, the middle part of the DNA fragment can be deleted and the two end parts can then be ligated together. The shortest DNA fragment is composed of only 60 bases after deletion. Generally, the polypeptide encoded by the deleted DNA fragment retains the features or characteristics of the thermophilic alkaline phosphatase.

The present invention also provides a recombinant vector which comprises one or more copies of the DNA fragment (or the deleted DNA fragment) of the invention. Said vector can be used to express the thermophilic alkaline phosphatase in host cells.

The vector includes eucaryotic vector and prokaryotic vector, preferably the prokaryotic vector so as to facilitate the amplification in prokaryote. The prokaryotic vector includes bacteriophage λ (such as λgtt11, λDash, λZapII, etc.) and plasmid (such as pBR322, pUC series, pBluescript, etc.). Plasmid is preferred. The above vectors are commercially available.

The present invention also provides a microorganism transformed by the recombinant vector of the invention. Gram-negative bacteria, especially E.Coli, are first recommended to be used as the host cells.

The recombinant vector of the invention can be obtained by using the following protocol:
(1) isolating the chromosome DNA from the prokaryotic organism, and digesting said DNA with an appropriate restriction endonuclease;
(2) integrating the digested DNA into a vector, using said recombinant vector to transform an appropriate host, and then constructing the gene library;
(3) screening the gene library of step (2) using an appropriate method;
(4) analyzing the positive clone screened out in step (3).

The chromosome DNA can be isolated by treating the prokaryote cells with lysozyme and then adding proteinase K.

The DNA can be digested using an appropriate restriction endonuclease according to the conventional molecular biology methods known in the art. The digested DNA is ligated into an appropriate clone vector, and the recombinant vector is used to transform appropriate organism to construct the gene library. The detailed description about these protocols can be found in laboratory manuals of gene engineering (Sambrook J, et al. In: Molecular Cloning, A Laboratory Manual. 2 ed., CSH Press, 1989).

The gene can be isolated by screening a library using the following methods: (A) hybridization using oligonucleotide probe; (B) polymerase chain reaction (PCR); (C) screening with a specific antibody; and (D) screening based on enzymatic activity. In situ hybridization with nucleic acid or oligonucleotide probes is a common method, however, screening based on enzymatic activity is preferred in the invention because it is easy to detect the activity of the thermophilic alkaline phosphatase. Moreover, the positive clones, which express the thermophilic alkaline phosphatase, can be screened in situ from colonies based on its thermostability.

The inserted DNA fragments in the positive clones can be bi-directionally sequenced by Sanger dideoxy-mediated chain termination method (conventional radioactive isotope manual sequencing or automatic sequencing by the automatic sequencing apparatus). The result is shown in FIG. 1.

The present invention also includes a method for producing the thermophilic alkaline phosphatase that is homologous or substantially homologous to the amino acid sequence shown in FIG. 1, which comprises:
(1) transforming the appropriate host cells with the DNA fragment (or partially deleted DNA fragment) encoding the enzyme of the invention or with a recombinant vector containing said DNA fragment;
(2) culturing the transformed host cells in the appropriate medium;
(3) isolating and purifying the protein from the cultured medium or the host cells.

The recombinant thermophilic alkaline phosphatase can be expressed under the control of any appropriate promoters and translation regulatory elements. The suitable hosts include the prokaryote, yeast, mammal cells, insect and plant, etc. The prokaryote is preferred and E.Coli is more preferred. The selection of vector depends on the particular host. In E.Coli, plasmids, such as pJLA503 (Lehauder B, et al. Gene, 1987; 53: 279–283) and pET series (a product available from Stratagene), are commonly used as the expression vector. Typically, the culture medium for E.Coli is abundant medium, such as 2×YT, etc. Based on the different vectors, the proteinase expression can be induced by changing the temperature or using a chemical method (such as using ITPG).

The thermophilic alkaline phosphatase can be isolated and purified from the cultured cells or medium. If the expressed enzyme protein is present inside the cells, the cells are centrifuged, then lysated by ultrasonic wave, lysozyme, or frozen-thaw cycles. The raw products can be obtained by centrifuging and filtering the cell lysate. If the enzyme protein is secreted into the medium, the enzyme can be obtained by centrifuging and removing the cells, and then purifying from the supernatant. There are many methods for the purification of the enzyme, such as salting-out, ultrafiltration, dialysis, ion-exchange chromatography, HPLC, etc. During the purification of the enzymes, the contaminated proteins can be eliminated effectively by incubating in an elevated temperature (such as 60° C.) for a period of time, which makes the purification procedure easier and more convenient.

The thermophilic alkaline phosphatase is useful for the labeling of nucleotides, proteins, or other biomacromolecules, and dephosphorizing the termini of DNA or RNA fragments in gene cloning. The primary use is to label nucleic acids or oligonucleotides directly. There are three main applications of labeled nucleic acids or oligonucleotides: (1) they can be used as the probes for nucleic acid hybridization and foot printing assay, including Southern blot, Northern blot, Slot blot, dot blot, Southern-western blot, hybridization in situ, etc.; (2) they can be used as the primers for nucleic acid amplification in vitro; (3) they can be used for DNA sequence analysis. The linkage between the enzyme protein and nucleic acids or oligonucleotides is a covalent bond established chemically or physically. The terminal group of nucleic acids or oligonucleotides can be linked to the amino group or hydrosulfide group of enzyme protein by a linker arm. (Ruth et al: DNA 1985; 4:93). The detection methods can be chemical, physical or biological methods. Depending on the solid-phase hybridization or the liquid-phase hybridization, the color visualization method using BCIP/NBT as a substrate or the chemiluminescent method using AMPPD as a substrate (Schaap A, et al. Clin Chem 1989, 35: 1863–1864) are preferred for the solid-phase hybridization; and pNPP is preferred as the substrate for liquid-phase hybridization. A quantitative assay may also be performed.

BRIEF DESCRIPTION OF THE DRAWINGS

FIGS. 1A, 1B, 1C, and 1D show the nucleotide sequence (SEQ ID NO:3) of the thermophilic alkaline phosphatase gene and its deduced amino acid sequence (SEQ ID NO:2). The sequence of amino acid expressed by three letters is listed under the DNA sequence. The underlined N-terminus of the amino acid sequence is a signal peptide composed of 26 amino acid residues.

DETAILED DESCRIPTION OF THE INVENTION

Figure 2:
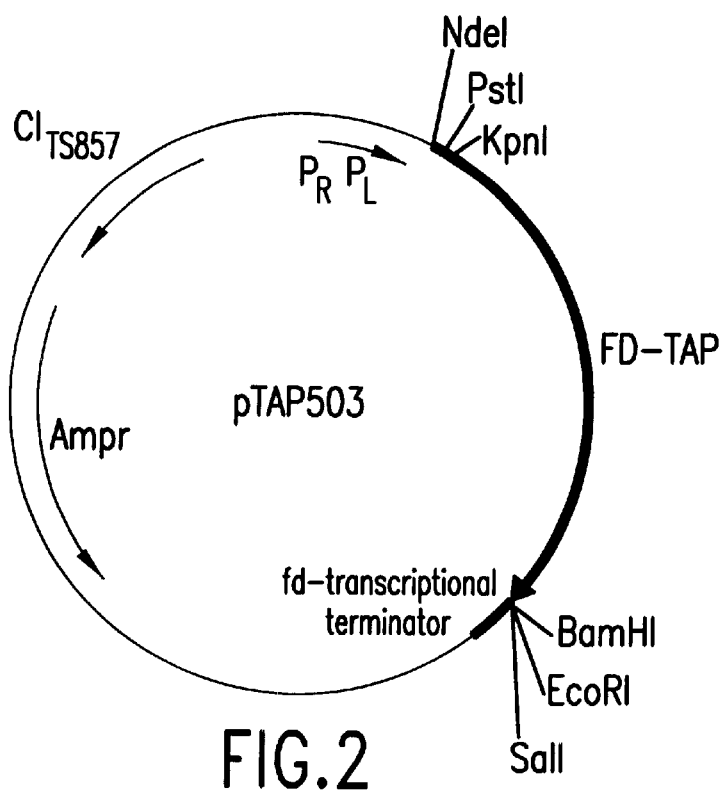
FIG. 2 shows the map of high expression plasmid pTAP503 containing FD-TAP gene.
Figure 3:
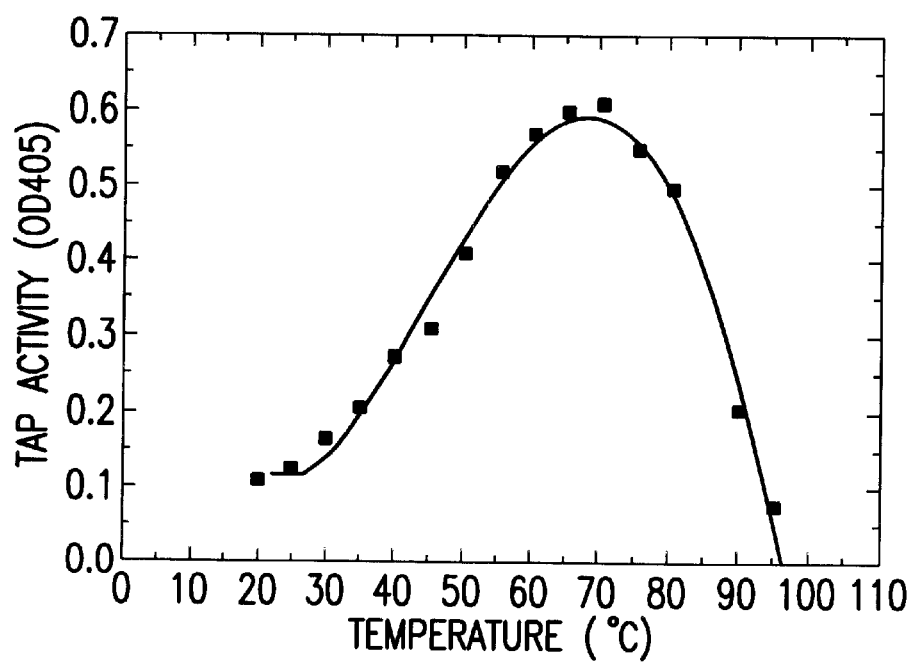
FIG. 3 shows the optimum temperature for FD-TAP.

The presetn invention is further elucidated by the examples, which are provided to describe the specific embodiments of the invention but are not to be construed as limiting the invention in any way.

The following abbreviations are used in the examples:
TE: 10 mmol/L Tris-HCl, 1 mmol/L EDTA, pH8.0
TH: 0.3% peptone, 0.3% yeast extract, 0.2% NaCl, pH7.0
LB: 1% peptone, 0.5% yeast extract, 1% NaCl, pH7.0
2×YT: 1.6% peptone, 1% yeast extract, 0.5% NaCl, pH7.0
FD-TAP: The thermophilic alkaline phosphatase derived from Thermus sp. FD3041.

EXAMPLE 1

Isolation of Chromosome DNA from Thermus sp. FD3041

Thermus sp. FD3041 (commercially available from Fu Hua Co., Ltd., Shanghai, China) was cultured in 200 ml of TH liquid medium at 70° C. The bacteria cells were harvested by centrifugation, suspended in 12 ml of TE buffer solution supplemented with 1 ml of TE buffer containing 10 mg/ml lysozyme, and then incubated in a water bath for 2 hours at 37° C. 1.5 ml of TE buffer containing 10% sodium dodecyl sarcosinate (Sarcosyl) and 1 mg/ml proteinase K was added and the resultant mixture was incubated at 37° C. for 1 hour. The mixture was extracted twice with phenol, and extracted twice with chloroform/isoamyl alcohol (24:1). 1/10 volume of 3 mol/L NaAc was added into the water phase. DNA was precipitated with 2 volumes of ethanol. The flocculent precipitate was reeled up with a glass stick, vacuum dried, and then dissolved in 3 nm TE buffer. 50 ul RNase A (10 mg/ml) was added. The chromosome DNA was extracted once with chloroform, precipitated with ethanol, and then dissolved in TE buffer.

EXAMPLE 2

Cloning of the DNA Fragment that Encodes the Thermostabe Alkaline Phosphatase 20 ug of chromosome DNA of Thermus sp. FD3041 was partially digested with enzyme Sau3AI. The 3–10 Kb DNA fragments were recovered by using low melting-point agarose electrophoresis. The two bases of the cohesive ends were partially filled in by using Klenow fragment and dGTP and DATP, so as to avoid self-ligation. The vector pUC118 was digested completely with enzyme Sal I. The larger fragment was recovered and the two bases of the cohesive ends were filled in using Klenow fragment and dCTP and dTTP. After filling-in, the cohesive ends of the chromosome DNA and the vector DNA were ligated together. After ligation with T4 ligase, the ligated DNA was used to transform E.Coli TG1. The white recombinant transformants were picked on LB plates containing ITPG, X-gal and ampicillin (100 ug/ml). Totally, 12,000 transformants were obtained, 85% of which contained 3–10 kb inserted fragments as confirmed by identifying the extracted plasmid. Thus, the chromosome gene library of Thermus sp. FD3041 was constructed.

The gene library was screened in situ by using the alkaline phosphatase color visualization method. The colonies were transferred onto a 3 mm filter paper. The paper was soaked in lysis buffer (1 mol/L diethanolamine, 1% SDS) and incubated at 85° C. for 10 mins, and then soaked in reaction buffer (6 mol/L pNPP, 1 mol/L diethanolamine, 1% SDS) at 70° C. for 10 mins. The positive colonies were those which turned yellow. After screening, five positive clones were isolated. For one clone (pTAP362), the physical map was constructed and TAP activity was tested for partially deleted plasmids. The FD-TAP was located in a 2 kb DNA fragment.

The DNA sequence was determined by using Sanger dideoxy-mediated chain-termination method, and a nucleotide sequence of 2030 bp was obtained (FIG. 1). According to computer analysis, the FD-TAP gene was 1506 bp in length with 68.2% of G+C% and encoded a proenzyme of 501 amino acid residues. For the third base of the codons, the G+C% was 92.7%, which was consistent with the characteristics of thermophilic bacteria gene. The 26 amino acid residues at the N-terminus of the proenzyme formed a signal peptide sequence and the mature enzyme was composed of 475 amino acid residues. FIG. 1 shows the DNA sequence of the FD-TAP gene and the amino acid sequence of its coded protein.

EXAMPLE 3

Subcloning and High Expression of the FD-TAP Gene

Primers were designed according to the sequences at the start codon and stop codon of FD-TAP gene. Nde I and BamH I site were introduced to the 5' end of the primers, respectively. The sequence of the mature FD-TAP gene was amplified by PCR, using pTAP118B plasmid as template. After digestion, the gene was cloned into the high expression vector pJLA503, and vector pJLA503 was used to transform E.Coli strain Mph44, which was defective in phoA gene. On the LB plate containing ampicillin, the recombinant transformants were screened in situ by using color visualization method. 50% of the transformants were positive for FD-TAP expression. For the recombinant plasmid in one clone (pTAP 503, FIG. 2), its DNA sequence was determined and the results showed that there was no mutation in the gene.

E.Coli Mph44 (pTAP503) was cultured in liquid medium at 30° C. and then induced at 42° C. for 10 hours. SDS-PAGE results showed an expressed enzyme of about 53 KDa. The recombinant protein was about 10% of the total proteins.

EXAMPLE 4

Isolation and Purification of the Recombinant FD-TAP Protein

E.coli Mph44 strain (pTAP503) was inoculated into 2×YT medium containing ampicillin 100 ug/ml. The bacteria was cultured in a shaker overnight at 30° C. to form a stock culture. This stock culture (2% of the final volume) was transferred into 2×YT medium and cultured in a shaker at 30° C. until the $A_{600}$, was 0.4–0.6, and then further cultured at 42° C. for 10 hours. bacteria cells were harvested by centrifugation and suspended in Buffer A (50 mmol/L Tris pH 8.8, glycerol, 10 mmol/L β-mercaptoethanol). The cells were lysed by supersonication in ice-water bath (total time= 400 seconds, pulse time=1 second, interval time=1 second, output power=25%). The lysate was centrifuged for 15 minutes at 15,000 rpm. The precipitate was discarded and the supernatant was collected. PEI was slowly added into the supernatant so that the final concentration PEI was 0.04% to remove the nucleic acids. After further centrifugation for 15 min at 15,000 rpm, the precipitate was discarded. To the supernatant, NaCl was added so that the final concentration of NaCl was 0.8 mmol/L. The supernatant was denatured by incubating in water bath at 70° C. for 30 minutes, centrifuged again for 15 minutes at 15,000 rpm to get rid of the non-thermotolerante contaminant proteins and the supernatant was collected. The solid ammonium sulfate was gradually added into the supernatant to reach the saturation concentration of 60% with stirring for 1 hour at 4° C. The supernatant was centrifuged for 20 minutes at 12,000 rpm. The supernatant was discarded and the precipitate was dissolved in ⅛ volume of Buffer B (10 mmol/L Na$_2$HPO$_4$—NaH$_2$PO$_4$, pH 6.8, glycerol, 10 mmol/L β-mercaptoethanol), and then dialyzed against the same buffer at 4° C. for desalting. After dialysis, the protein sample was subject to ion-exchange chromatography using CM sepharose Flast Flow column. After the sample was loaded, the column was eluted with Buffer B until A280 nm absorbance was back to basal level. The elution was further performed with NaCl linear gradient solution (0~0.5 mol/L). The eluate fractions were collected with 1.5 ml per tube. The purity of the protein was analyzed using SDS-PAGE. The purified protein peak fractions were pooled, lyophilized and stored at −20° C.

EXAMPLE 5
The Enzyme Activity and Characteristics of FD-TAP Protein 10 ul of enzyme solution was added into 1000 ul reaction system (6 mmol/L pNPP, 1 mol/L diethanolamine, pH 11.6). After incubating at 70° C. for 10 minutes, 990 μl of trichloroacetic acid was added to stop the reaction. The absorbance at 405 nm (OD$_{405}$) of the resultant product was determined on UV260 apparatus. The unit of enzyme activity was defined as follows: one unit was defined as the amount of enzyme required to produce 1 μmol/L NPP per minute at 70° C., pH 11.6. Enzyme unit=A405×2/(18.8×10), in which 2 stands for total reaction volume, 10 for reaction time and the molar extinction coefficient of NPP at 405 nm is 18.8×10$^6$.

Some enzymological properties of FD-TAP:

Optimum reaction temperature: 70° C.

Figure 4:
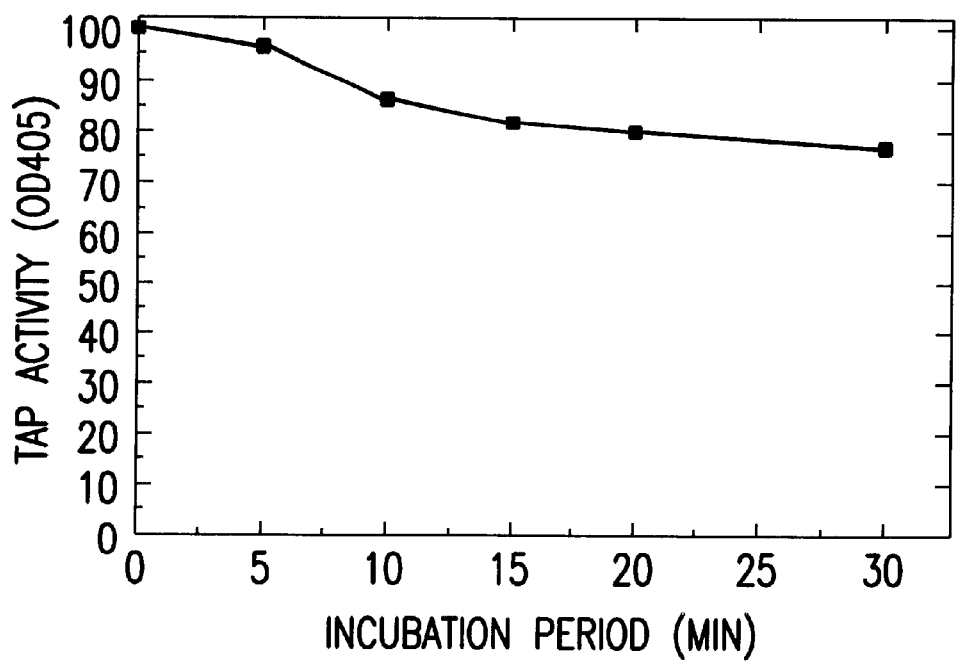
FIG. 4 shows the thermostability of FD-TAP. The enzyme activity was measured at 70° C. after incubating the enzyme solution at 95° C. for a different period of time.

Thermo-tolerance: The enzyme was solved in a system (50 mmol/L Tris, pH 8.8, 25° C.). After incubating at 95° C. for 30 minutes, the enzyme activity remained more than 90% (FIG. 4).

Figure 5:
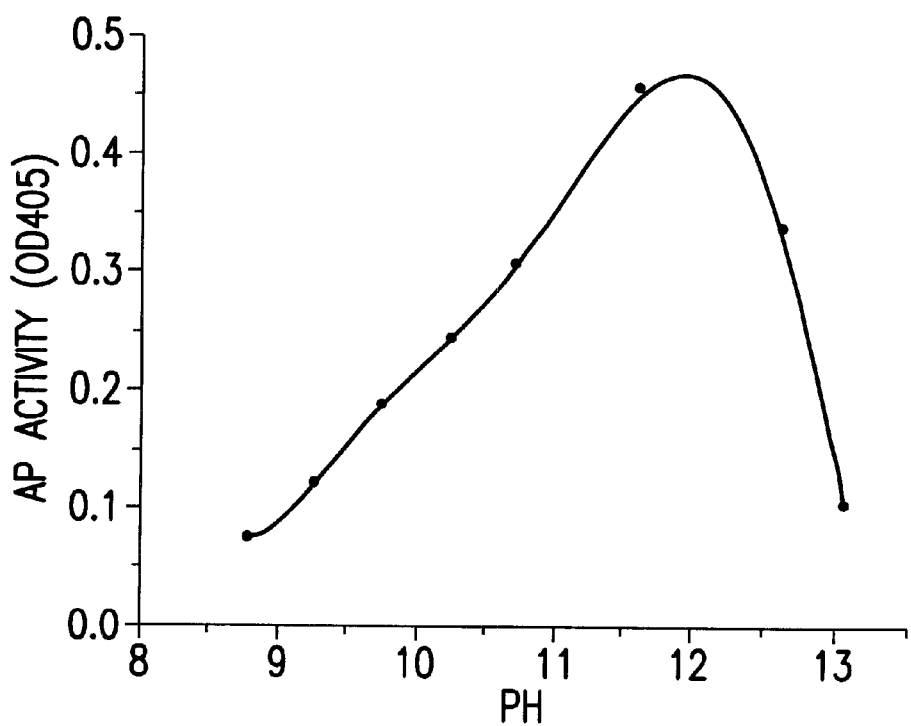
FIG. 5 shows the effect of pH on FD-TAP activity.

Optimum pH: pH 12 (FIG. 5).

EXAMPLE 6
Partial Deletion of FD-TAP Gene

The primers were designed according to the sequences at different positions of FD-TAP gene. The DNA fragments with different sizes were amplified: 79→1506, 79→1416, 79→960, 271→480, 271→330. NdeI site was introduced to the 5' end of upstream primers, stop codon and BamH I site were introduced to downstream primers. The desired fragments were amplified by PCR, using pTAP118B plasmid as template. These amplified DNA fragments were cloned into high expression vector pJLA503, which was used to transform E.Coli Mph44. The transformants were screened to obtain the positive colonies containing the DNA fragments mentioned above. Expression of the protein was induced and the recombinant polypeptides were isolated and purified. The enzymological properties of said polypetieds were studied. The results showed that these polypeptides had properties and characteristics similar to those of the intact FD-TAP.

What is claimed is:

1. An isolated thermophilic alkaline phosphatase having the amino acid sequence of SEQ ID NO:2.

2. The thermophilic alkaline phosphatase of claim 1 wherein said alkaline phosphatase is encoded by a nucleic acid sequence of SEQ ID NO:1.

3. A recombinant and/or isolated thermophilic alkaline phosphoesterase comprising a polypeptide having the amino acid sequence of residues 1–475 of SEQ ID NO:2.

4. The thermophilic alkaline phosphatase of claim 3, wherein said alkaline phosphatase has a temperature optimum above 5° C. and retains at least 70% of the activity of an alkaline phosphatase having the amino acid sequence of SEQ ID NO:2 after incubation at 70° C. for about 30 minutes.

5. The thermophilic alkaline phosphatase of claim 4, wherein said alkaline phosphatase is encoded by a nucleic acid sequence of SEQ ID NO:1.

* * * * *

SEQUENCE LISTING

```
<160> NUMBER OF SEQ ID NOS: 3

<210> SEQ ID NO 1
<211> LENGTH: 1506
<212> TYPE: DNA
<213> ORGANISM: Thermus
<220> FEATURE:
<221> NAME/KEY: CDS
<222> LOCATION: (1)...(1506)
<223> OTHER INFORMATION: encodes a thermophilic alkaline phosphoesterase
<221> NAME/KEY: sig_peptide
<222> LOCATION: (1)...(78)
<223> OTHER INFORMATION: encodes a signal peptide

<400> SEQUENCE: 1
atgaagcgaa gggacatcct gaaaggtggc ctggctgcgg gggccctggc cctcctgccc      60
cggggccata cccaggggc tctgcagaac cagccttcct tgggaaggcg gtaccgcaac      120
ctcatcgtct tcgtctacga cgggttttcc tgggaggact acgccatcgc ccaggcctac      180
gcccggaggc ggcagggccg ggttctcgcc ctggagcgcc tcctcgcccg ctacccaac      240 gggctcatca acacctacag cctcaccagc tacgtcaccg agtccagcgc cgcggggaac      300
gccttctcct gcggggtgaa gacggtgaac gggggctcg ccatccacgc cgacgggacc      360
cccctcaagc ccttcttcgc cgcggccaag gaggcgggga aggccgtggg gctcgtgacc      420
accaccaccg tcacccacgc caccccggcg agcttcgtgg tgtccaatcc cgaccggaac      480
gccgaggaga ggatcgccga gcagtacctg gagttcgggg ccgaggtgta ccttgggggc      540
ggggaccgct ttttcaaccc cgccaggcgc aaggacggga aggacctcta cgccgccttc      600
```

-continued

```
gccgccaagg ggtacggggt ggtgcgcacc cccgaggagc tcgcccgttc caacgccacc      660
cggctcctgg gcgtcttcgc cgacggccac gtgccctacg agattgaccg ccgcttccag      720
ggccttgggg tgccgagcct caaggaaatg gtccaggccg ctttgccccg gcttgccgcc      780
caccgcgggg gcttcgtcct tcaggtggaa gcggggcgga ttgaccacgc caaccatttg      840
aacgacgccg gggccaccct ttgggacgtg ctggcggcg acgaggtctt ggagcttctc       900
accgccttcg tggaccggaa cccggacacc ctcctcctcg tggtctcgga ccacgccacc      960
ggggtggggg ccctctacgg ggcgggccgg agctacctgg agagctccgt gggcattgac     1020
ctcctggggg cgcaaaaggc cagctttgag tacatgcgcc gcgtcttggg ctcggccccc     1080
gatgctgccc aggtgaagga ggcctaccag accctgaagg gggtctccct cacggacgag     1140
gaggcgcaga tggtggtccg ggccatccgc gagcgggtct actggcctga tgccgtgcgc     1200
cagggcatcc agcccgaaaa caccatggcc tgggccatgg tgcagaagaa cgccagcaag     1260
cccgaccggc ccaacatcgg ctggagctct gggcagcaca cggcgagccc cgtcatcctc     1320
ctcctctacg ccagggcct gcgcttcgtc cagcttggcc tggtggacaa cacccacgtg      1380
ttccgcctga tgggcgaggc cctgaacctc cgctaccaga accggtgat gagcgaggag      1440 gaggccctgg agatcctcaa ggccaggccc caggggatgc cccaccccga ggacgtctgg     1500
gcctaa                                                                1506
```

<210> SEQ ID NO 2
<211> LENGTH: 501
<212> TYPE: PRT
<213> ORGANISM: Thermus sp. FD3041
<220> FEATURE:
<221> NAME/KEY: SIGNAL
<222> LOCATION: (1)...(26)
<223> OTHER INFORMATION: Signal peptide

<400> SEQUENCE: 2

```
Met Lys Arg Arg Asp Ile Leu Lys Gly Gly Leu Ala Ala Gly Ala Leu
    -25                 -20                 -15

Ala Leu Leu Pro Arg Gly His Thr Gln Gly Ala Leu Gln Asn Gln Pro
-10              -5                   1               5

Ser Leu Gly Arg Arg Tyr Arg Asn Leu Ile Val Phe Val Tyr Asp Gly
             10                  15                  20

Phe Ser Trp Glu Asp Tyr Ala Ile Ala Gln Ala Tyr Ala Arg Arg Arg
         25                  30                  35

Gln Gly Arg Val Leu Ala Leu Glu Arg Leu Leu Ala Arg Tyr Pro Asn
     40                  45                  50

Gly Leu Ile Asn Thr Tyr Ser Leu Thr Ser Tyr Val Thr Glu Ser Ser
55                  60                  65                  70

Ala Ala Gly Asn Ala Phe Ser Cys Gly Val Lys Thr Val Asn Gly Gly
                75                  80                  85

Leu Ala Ile His Ala Asp Gly Thr Pro Leu Lys Pro Phe Phe Ala Ala
                90                  95                 100

Ala Lys Glu Ala Gly Lys Ala Val Gly Leu Val Thr Thr Thr Thr Val
            105                 110                 115

Thr His Ala Thr Pro Ala Ser Phe Val Val Ser Asn Pro Asp Arg Asn
        120                 125                 130

Ala Glu Glu Arg Ile Ala Glu Gln Tyr Leu Glu Phe Gly Ala Glu Val
    135                 140                 145                 150

Tyr Leu Gly Gly Gly Asp Arg Phe Phe Asn Pro Ala Arg Arg Lys Asp
```

```
                    155                 160                 165
Gly Lys Asp Leu Tyr Ala Ala Phe Ala Ala Lys Gly Tyr Gly Val Val
                170                 175                 180

Arg Thr Pro Glu Glu Leu Ala Arg Ser Asn Ala Thr Arg Leu Leu Gly
            185                 190                 195

Val Phe Ala Asp Gly His Val Pro Tyr Glu Ile Asp Arg Arg Phe Gln
        200                 205                 210

Gly Leu Gly Val Pro Ser Leu Lys Glu Met Val Gln Ala Ala Leu Pro
215                 220                 225                 230

Arg Leu Ala Ala His Arg Gly Phe Val Leu Gln Val Glu Ala Gly
                235                 240                 245

Arg Ile Asp His Ala Asn His Leu Asn Asp Ala Gly Ala Thr Leu Trp
            250                 255                 260

Asp Val Leu Ala Ala Asp Glu Val Leu Glu Leu Leu Thr Ala Phe Val
        265                 270                 275

Asp Arg Asn Pro Asp Thr Leu Leu Val Val Ser Asp His Ala Thr
    280                 285                 290

Gly Val Gly Ala Leu Tyr Gly Ala Gly Arg Ser Tyr Leu Glu Ser Ser
295                 300                 305                 310

Val Gly Ile Asp Leu Leu Gly Ala Gln Lys Ala Ser Phe Glu Tyr Met
                315                 320                 325

Arg Arg Val Leu Gly Ser Ala Pro Asp Ala Ala Gln Val Lys Glu Ala
            330                 335                 340

Tyr Gln Thr Leu Lys Gly Val Ser Leu Thr Asp Glu Glu Ala Gln Met
        345                 350                 355

Val Val Arg Ala Ile Arg Glu Arg Val Tyr Trp Pro Asp Ala Val Arg
    360                 365                 370

Gln Gly Ile Gln Pro Glu Asn Thr Met Ala Trp Ala Met Val Gln Lys
375                 380                 385                 390

Asn Ala Ser Lys Pro Asp Arg Pro Asn Ile Gly Trp Ser Ser Gly Gln
                395                 400                 405

His Thr Ala Ser Pro Val Ile Leu Leu Tyr Gly Gln Gly Leu Arg
            410                 415                 420

Phe Val Gln Leu Gly Leu Val Asp Asn Thr His Val Phe Arg Leu Met
        425                 430                 435

Gly Glu Ala Leu Asn Leu Arg Tyr Gln Asn Pro Val Met Ser Glu Glu
    440                 445                 450

Glu Ala Leu Glu Ile Leu Lys Ala Arg Pro Gln Gly Met Arg His Pro
455                 460                 465                 470

Glu Asp Val Trp Ala
                475

<210> SEQ ID NO 3
<211> LENGTH: 2030
<212> TYPE: DNA
<213> ORGANISM: Thermus sp. FD3041
<220> FEATURE:
<221> NAME/KEY: CDS
<222> LOCATION: (82)...(1587)
<223> OTHER INFORMATION: encodes a thermophilic alkaline phosphoesterase

<400> SEQUENCE: 3
gccttcccag ggtcacgggg tcattatccc ctgaccttcc cctgacttgc gctccttact      60
ttgaactcgg aggtgagaag c atg aag cga agg gac atc ctg aaa ggt ggc     111
                        Met Lys Arg Arg Asp Ile Leu Lys Gly Gly
                          1               5                  10
```

-continued

| | |
|---|---|
| ctg gct gcg ggg gcc ctg gcc ctc ctg ccc cgg ggc cat acc cag ggg<br>Leu Ala Ala Gly Ala Leu Ala Leu Leu Pro Arg Gly His Thr Gln Gly<br>                    15                    20                  25 | 159 |
| gct ctg cag aac cag cct tcc ttg gga agg cgg tac cgc aac ctc atc<br>Ala Leu Gln Asn Gln Pro Ser Leu Gly Arg Arg Tyr Arg Asn Leu Ile<br>         30                    35                    40 | 207 |
| gtc ttc gtc tac gac ggg ttt tcc tgg gag gac tac gcc atc gcc cag<br>Val Phe Val Tyr Asp Gly Phe Ser Trp Glu Asp Tyr Ala Ile Ala Gln<br>               45                   50                  55 | 255 |
| gcc tac gcc cgg agg cgg cag ggc cgg gtt ctc gcc ctg gag cgc ctc<br>Ala Tyr Ala Arg Arg Arg Gln Gly Arg Val Leu Ala Leu Glu Arg Leu<br>60                         65                       70 | 303 |
| ctc gcc cgc tac ccc aac ggg ctc atc aac acc tac agc ctc acc agc<br>Leu Ala Arg Tyr Pro Asn Gly Leu Ile Asn Thr Tyr Ser Leu Thr Ser<br>75                       80                     85                  90 | 351 |
| tac gtc acc gag tcc agc gcc gcg ggg aac gcc ttc tcc tgc ggg gtg<br>Tyr Val Thr Glu Ser Ser Ala Ala Gly Asn Ala Phe Ser Cys Gly Val<br>               95                  100                 105 | 399 |
| aag acg gtg aac ggg ggg ctc gcc atc cac gcc gac ggg acc ccc ctc<br>Lys Thr Val Asn Gly Gly Leu Ala Ile His Ala Asp Gly Thr Pro Leu<br>        110                    115                 120 | 447 |
| aag ccc ttc ttc gcc gcg gcc aag gag gcg ggg aag gcc gtg ggg ctc<br>Lys Pro Phe Phe Ala Ala Ala Lys Glu Ala Gly Lys Ala Val Gly Leu<br>        125                    130                 135 | 495 |
| gtg acc acc acc gtc acc cac gcc acc ccg gcg agc ttc gtg gtg<br>Val Thr Thr Thr Thr Val Thr His Ala Thr Pro Ala Ser Phe Val Val<br>        140                    145                 150 | 543 |
| tcc aat ccc gac cgg aac gcc gag gag agg atc gcc gag cag tac ctg<br>Ser Asn Pro Asp Arg Asn Ala Glu Glu Arg Ile Ala Glu Gln Tyr Leu<br>155                       160                 165                 170 | 591 |
| gag ttc ggg gcc gag gtg tac ctt ggg ggc ggg gac cgc ttt ttc aac<br>Glu Phe Gly Ala Glu Val Tyr Leu Gly Gly Gly Asp Arg Phe Phe Asn<br>               175                  180                 185 | 639 |
| ccc gcc agg cgc aag gac ggg aag gac ctc tac gcc gcc ttc gcc gcc<br>Pro Ala Arg Arg Lys Asp Gly Lys Asp Leu Tyr Ala Ala Phe Ala Ala<br>        190                    195                 200 | 687 |
| aag ggg tac ggg gtg gtg cgc acc ccc gag gag ctc gcc cgt tcc aac<br>Lys Gly Tyr Gly Val Val Arg Thr Pro Glu Glu Leu Ala Arg Ser Asn<br>        205                    210                 215 | 735 |
| gcc acc cgg ctc ctg ggc gtc ttc gcc gac ggc cac gtg ccc tac gag<br>Ala Thr Arg Leu Leu Gly Val Phe Ala Asp Gly His Val Pro Tyr Glu<br>220                       225                 230 | 783 |
| att gac cgc cgc ttc cag ggc ctt ggg gtg ccg agc ctc aag gaa atg<br>Ile Asp Arg Arg Phe Gln Gly Leu Gly Val Pro Ser Leu Lys Glu Met<br>235                       240                 245                 250 | 831 |
| gtc cag gcc gct ttg ccc cgg ctt gcc gcc cac cgc ggg ggc ttc gtc<br>Val Gln Ala Ala Leu Pro Arg Leu Ala Ala His Arg Gly Gly Phe Val<br>        255                    260                 265 | 879 |
| ctt cag gtg gaa gcg ggg cgg att gac cac gcc aac cat ttg aac gac<br>Leu Gln Val Glu Ala Gly Arg Ile Asp His Ala Asn His Leu Asn Asp<br>        270                    275                 280 | 927 |
| gcc ggg gcc acc ctt tgg gac gtg ctg gcg gcg gac gag gtc ttg gag<br>Ala Gly Ala Thr Leu Trp Asp Val Leu Ala Ala Asp Glu Val Leu Glu<br>        285                    290                 295 | 975 |
| ctt ctc acc gcc ttc gtg gac cgg aac ccg gac acc ctc ctc ctc gtg<br>Leu Leu Thr Ala Phe Val Asp Arg Asn Pro Asp Thr Leu Leu Leu Val<br>300                       305                 310 | 1023 |
| gtc tcg gac cac gcc acc ggg gtg ggg gcc ctc tac ggg gcg ggc cgg<br>Val Ser Asp His Ala Thr Gly Val Gly Ala Leu Tyr Gly Ala Gly Arg | 1071 |

-continued

```
315              320              325              330
agc tac ctg gag agc tcc gtg ggc att gac ctc ctg ggg gcg caa aag    1119
Ser Tyr Leu Glu Ser Ser Val Gly Ile Asp Leu Leu Gly Ala Gln Lys
                335              340              345 gcc agc ttt gag tac atg cgc cgc gtc ttg ggc tcg gcc ccc gat gct    1167
Ala Ser Phe Glu Tyr Met Arg Arg Val Leu Gly Ser Ala Pro Asp Ala
                350              355              360 gcc cag gtg aag gag gcc tac cag acc ctg aag ggg gtc tcc ctc acg    1215
Ala Gln Val Lys Glu Ala Tyr Gln Thr Leu Lys Gly Val Ser Leu Thr
            365              370              375 gac gag gag gcg cag atg gtg gtc cgg gcc atc cgc gag cgg gtc tac    1263
Asp Glu Glu Ala Gln Met Val Val Arg Ala Ile Arg Glu Arg Val Tyr
        380              385              390 tgg cct gat gcc gtg cgc cag ggc atc cag ccc gaa aac acc atg gcc    1311
Trp Pro Asp Ala Val Arg Gln Gly Ile Gln Pro Glu Asn Thr Met Ala
395              400              405              410 tgg gcc atg gtg cag aag aac gcc agc aag ccc gac cgg ccc aac atc    1359
Trp Ala Met Val Gln Lys Asn Ala Ser Lys Pro Asp Arg Pro Asn Ile
                415              420              425 ggc tgg agc tct ggg cag cac acg gcg agc ccc gtc atc ctc ctc ctc    1407
Gly Trp Ser Ser Gly Gln His Thr Ala Ser Pro Val Ile Leu Leu Leu
                430              435              440 tac ggc cag ggc ctg cgc ttc gtc cag ctt ggc ctg gtg gac aac acc    1455
Tyr Gly Gln Gly Leu Arg Phe Val Gln Leu Gly Leu Val Asp Asn Thr
            445              450              455 cac gtg ttc cgc ctg atg ggc gag gcc ctg aac ctc cgc tac cag aac    1503
His Val Phe Arg Leu Met Gly Glu Ala Leu Asn Leu Arg Tyr Gln Asn
        460              465              470 ccg gtg atg agc gag gag gag gcc ctg gag atc ctc aag gcc agg ccc    1551
Pro Val Met Ser Glu Glu Glu Ala Leu Glu Ile Leu Lys Ala Arg Pro
475              480              485              490 cag ggg atg cgc cac ccc gag gac gtc tgg gcc taa gggcgggtcg         1597
Gln Gly Met Arg His Pro Glu Asp Val Trp Ala  *
                495              500 cgggatcggc cggggccggt tgggtccgt gggagccggg cttttggctt cctgggcggg    1657
aaccttgccc ccgccgaggc agggccgccc cgccaccagg aggtaggcct cctgagccgc   1717
ctcggccaaa agggcgttca cctggcccag gaggtcccgg tagcggcggg cgaggggtt    1777 ttgggggacg atccccatcc ccacctcgtt ggagacggcg atgaccctct tgccgctttc   1837
ctccaccgcg cttaggaagc gcctcgcctc caagaggggg tccaggcccc gttccatcag   1897 gttgcgaac ccagagggtg aggcagtcca ccaccacggt ggggtggcgg gccctctta    1957 gggcccccgg gaggtccagg ggctcctcca gggtctccca ggtgggggg cgctcctcct    2017 ggtgggcggc gga                                                     2030
```